United States Patent [19]

Sato

[11] Patent Number: 4,991,777

[45] Date of Patent: Feb. 12, 1991

[54] NOZZLE MEMBER IN USE WITH A JET SHOOTING DEVICE

[76] Inventor: Hiromichi Sato, 3-21-403, Kita-machi 2-chome, Nerima-ku, Tokyo, Japan

[21] Appl. No.: 276,743

[22] Filed: Nov. 28, 1988

[30] Foreign Application Priority Data

Nov. 30, 1987 [JP] Japan .................................. 62-302922

[51] Int. Cl.⁵ .............................................. A61M 31/00
[52] U.S. Cl. .................................... 239/327; 239/543; 239/601; 222/215; 604/275
[58] Field of Search ........................ 604/275, 279, 37; 239/543, 544, 601, 433, 327, 596–598; 222/206, 207, 210, 211, 215

[56] References Cited

U.S. PATENT DOCUMENTS

| 2,674,247 | 4/1954 | McLellan | 239/327 |
| 2,945,739 | 7/1960 | Lehmicke | 239/601 |
| 3,082,961 | 3/1963 | Hruby | 239/598 |
| 3,406,913 | 10/1968 | Frangos | 239/543 |
| 3,568,933 | 3/1971 | Macguire-Cooper | 239/543 |

FOREIGN PATENT DOCUMENTS

| 549465 | 10/1956 | France | 239/597 |
| 1407566 | 7/1988 | U.S.S.R. | 239/597 |

*Primary Examiner*—Andres Kashnikow
*Assistant Examiner*—Kevin P. Weldon
*Attorney, Agent, or Firm*—Varndell Legal Group

[57] ABSTRACT

A nozzle member is disclosed. A jet nozzle includes a pair of circular holes of the same diameters, and a slit-like hole of the width at least equal to or shorter than the diameter of the paired holes, through which the paired holes intercommunicate with each other. A jet medium jetted from the nozzle becomes a spirally turning strip of jet medium at the start of its jetting. The spirally turning force of the jet medium is maintained with little attenuation during the course of its travel. The projected strip of jet medium hits an object concentrically, not dissipatedly.

9 Claims, 6 Drawing Sheets

NOZZLE MEMBER IN USE WITH A JET SHOOTING DEVICE

BACKGROUND ART

The present invention relates to a nozzle member in use with a jet shooting device for concentrically shooting forth a jet of liquid, for example, water or a jet of gas, for example, air, toward an object. More particularly, the present invention relates to a nozzle member in use with an anal washer.

Figure 13:
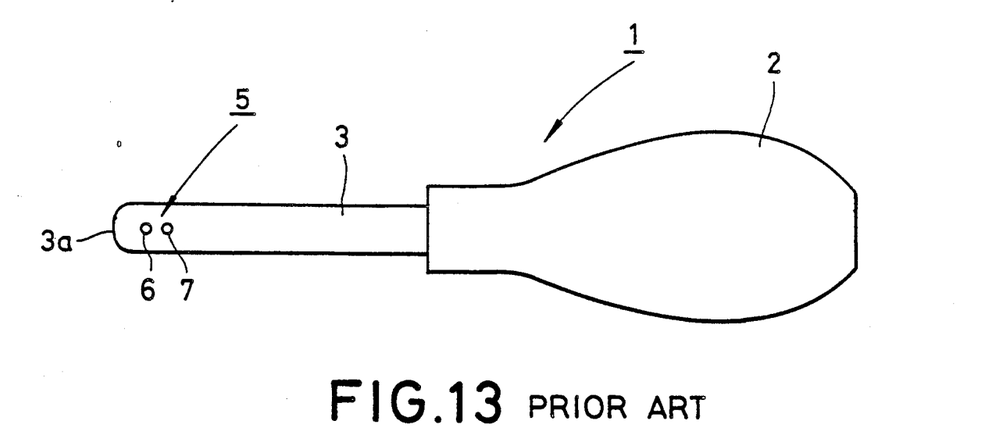
FIG. 13 is a schematic perspective view showing a conventional jet shooting device.

FIG. 13 is a plan view showing a conventional jet shooting device or sprayer as proposed by the applicant of the present patent application, and disclosed in Japanese Utility Model Application Laid-Open Publication No. 58-8023 5. This shooting device 1, which is a jet shooting device as developed mainly for washing particularly an anal of a piles patient, is made up of a container 2, which is made of rigid macromolecular material and contains a washing liquid, such as hot water, and a tubular nozzle member 3 coupled with the container 1. The container 1 is shaped like a gourd and opened at one end, and made of flexibly deformable, resilient material. The nozzle member 3 is screwed onto the open end of the container 2, and fastened thereto.

The nozzle member 3 is constructed with a tubular member of which one end 3a is closed and the other end is opened. A jet nozzle 5 is formed in the circumferential surface of the end portion 3a of the nozzle member 3. The nozzle 5 consists of a couple of slender through-holes 6 and 7 apart from each other at a predetermined distance. The through-holes 6 and 7 are formed so that their axial lines 6a and 7a are inclined, and intersect and cross at point P located outside the jet nozzle member 3, as shown in FIG. 14 showing an enlarged, sectional view of a key portion of the nozzle member 3.

Figure 14:
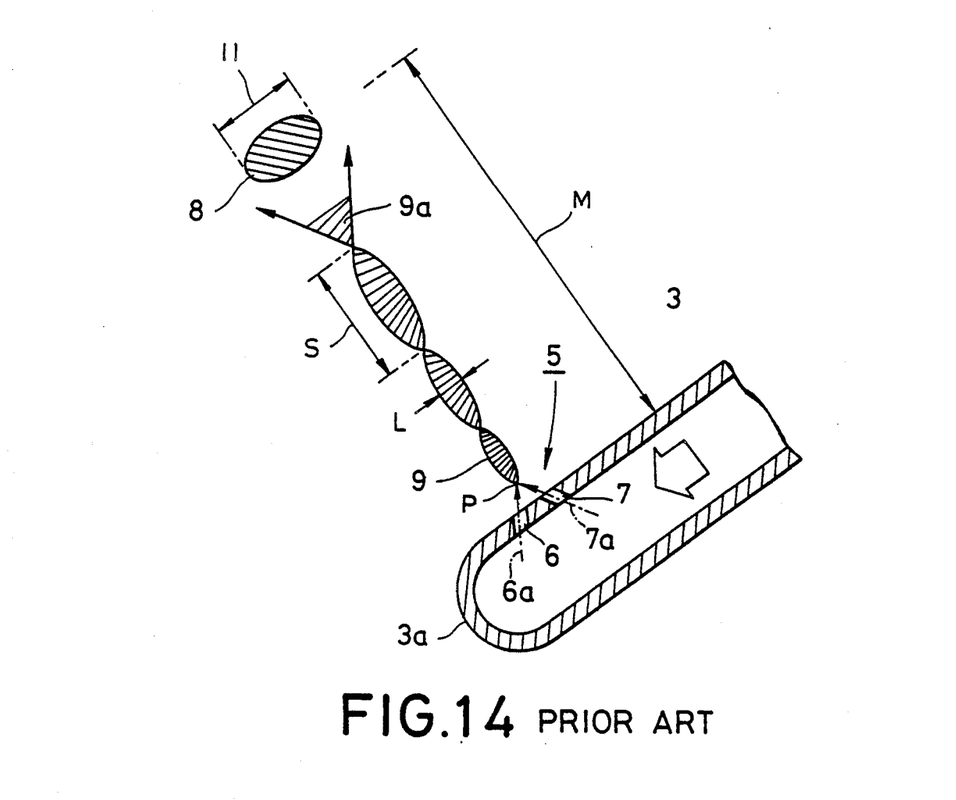
FIG. 14 is an enlarged sectional view of a key portion of the jet shooting device of FIG. 13.

To use the jet shooting device 1 thus constructed, the jet nozzle 5 of the nozzle member 3 is set under and in alignment with an object 8 (e.g., anal), as shown in FIG. 14. Then, an operator forcefully grasps and presses the container 1 containing washing medium (hot water at about 40° C., in this instance) to deform it. In turn, the resultant high pressure hot water within the nozzle member 3 is shot from the pair of holes 6 and 7 toward the object. At this time, as indicated by an arrow, a pair of water streams emitted from the holes 6 and 7 contact and cross at point P outside the nozzle member 3, and these water streams interact with each other to be a strip-like jet, which travels while spirally turning. The strip of jet, with improved straight drive, is forcefully projected toward the object 8. When the object 8 is hit with the spirally turning jet strip 9 in this way, the concentration of the jet at the object and the washing power of the jet when it washes the object (anal) are improved over those when the object is shot by the jet with no spiral rotation.

In the above nozzle member, the through-holes 6 and 7 are inclined such that a pair of linear streams of jet medium projected from those holes 6 and 7 cross at point P outside nozzle member 3. When the jets intersect at external point P, the kinetic energy of the jet medium is greatly lost, and consequently the turning force of the spirally travelling jet is remarkably reduced. Finally, the pitch S and the width L of the jet 9 having a strip-like shape and traveling while spirally turning, gradually increases. At the leading end 9a of the jet 9, the jet strip broadly expands, or loses its concentration.

An experiment was conducted by the nozzle member under discussion in the following condition: distance M between the nozzle member surface and the object 8 is 1 m; the diameter of each of the paired holes 6 and 7, 1.2 mm; and pitch between the holes 15 and 16, about 2.0 mm. Under this condition, the container 1 was forcefully grasped to press the contained medium and shoot forth the jet 9 toward the object 8. The result of the experiment showed that the width N of the jet strip 9 was approximately 20 mm at a place of the object 8, and that the jet 9 greatly expanded at the leading end 9a.

The above fact shows that the jet shooting device 1 for shooting forward a washing liquid, which was devised mainly for washing an anal and described above, is incapable of concentrically shooting forth the jet 9 toward the object (anal), and since the turning force of the jet 9 is greatly attenuated, the washing power for the object 8 is reduced. This is one of the major problems of the conventional nozzle member for the jet shooting device.

Another problem arises from the slanted holes 6 and 7 forming the jet nozzle 5 in the nozzle member 3. Those slanted holes cannot be punched by a metal mold. Therefore, it is impossible to form the whole nozzle member 3 including the jet nozzle 5, in one manufacturing step. An additional step to punch the structure must be used for forming the slanted holes 6 and 7. Thus, the conventional nozzle member 3 requires an increased number of manufacturing steps. Further, the punching work is difficult because it must be performed in a slanted state at a predetermined angle. The result is degradation of the production yield, and expensiveness of the manufactured jet shooting device.

SUMMARY OF THE INVENTION

With the view of solving the problems involved in the conventional jet shooting device, the present invention has an object to provide a jet shooting device which shoots forth a jet toward an object concentrically, not dissipatedly.

The present invention has another object to provide a jet shooting device which shoots forth a jet toward an object concentrically, not dissipatedly, and requires a simple manufacturing process.

To achieve the above object, in a jet shooting device according to the present invention, a jet nozzle of a nozzle member includes a pair of circular holes of the same diameters, and a slit-like hole of the width at least equal to or shorter than the diameter of said paired holes, through which said paired holes intercommunicate with each other. Further, the longitudinal section of each of these holes is substantially orthogonal to the circumferential surface of the nozzle member.

With the thus constructed nozzle member, the jet medium jetted from the the nozzle member becomes a spirally turning strip of jet medium at the start of its jetting, and travels with little attenuation of the turning force. Therefore, the stream of jet medium may be concentrically shot forth toward an object, and will never dissipate during the course of its travel.

Other objects, features, and advantages of the present invention will be apparent when carefully reading the following detailed description in conjunction with the accompanying drawings, in which:

BEST MODE FOR CARRYING OUT THE INVENTION

An embodiment of a nozzle member according to the present invention will be described in detail with reference to the accompanying drawings.

Figure 1:
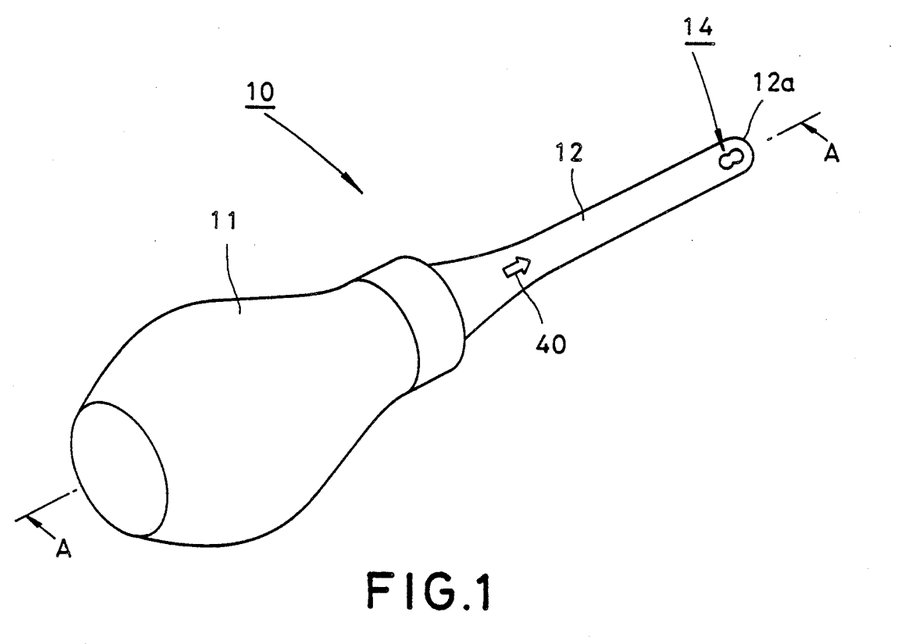
FIG. 1 is a schematic perspective view showing a jet shooting device according to the present invention.

FIG. 1 is a schematic perspective view showing a jet shooting device 10 according to the present invention. In this embodiment, the present invention is applied to a jet shooting device for shooting forth a jet of washing liquid mainly for washing an anal, like the conventional jet shooting device.

This shooting device 10 is made up of a container 11 containing a washing liquid, such as hot water, particularly for washing an anal of a piles patient, and a tubular jet nozzle member 12 coupled with the container 11. The container 11 is shaped like a gourd and opened at one end, and made of flexibly deformable, resilient material. The tubular nozzle member 12 is made of rigid macromolecular material.

Figure 2:
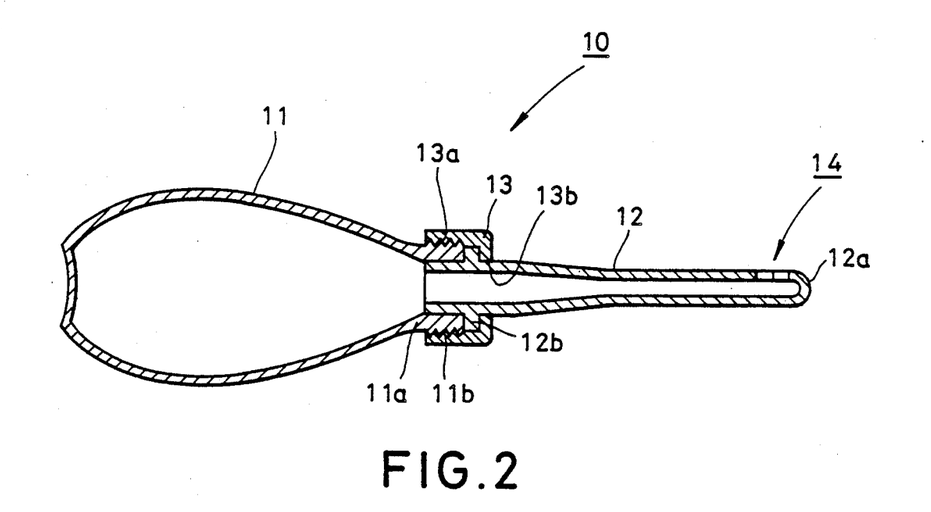
FIG. 2 is a longitudinal sectional view taken on line A—A in FIG. 1.

As well illustrated in FIG. 2 showing a longitudinal sectional view taken on line A—A in FIG. 1, an external thread 11b is formed around an end portion 11a of the container 11. A cap 13 having an internal thread 13a on the internal circumferential surface is screwed onto the external thread 11b. This cap 13 is used for securing the nozzle member 12 to the opening end 11a of the container 11. To secure the nozzle member 12 to the opening end 11a of the container 11, a closed end portion 12a of the nozzle member 12 is inserted into a hole 13b centered in the cap 13 till a flange 12b of the nozzle member 12 engages with the cap 13. Then, the cap 13 is screwed onto the container 11, so that by a fastening force generated between the cap 13 and the container 11, the flange 12b is firmly pressed against the container 11, and consequently the nozzle member 12 and the container 11 are firmly coupled with each other.

Figure 3:
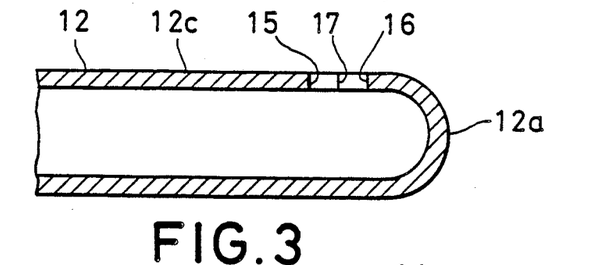
FIG. 3 is a sectional view of a diagram of FIG. 4.

As shown in FIGS. 1 and 2, a jet nozzle 14 is formed in the end portion 12a of the nozzle member 12. This nozzle 14 includes a pair of round holes 15 and 16 of the same diameters, and a slit-like hole 17 whose width W is at least equal to or shorter than the diameter F of each hole 15 and 16, through which the paired holes 15 and 16 intercommunicate with each other. As shown in FIG. 3 as an enlarged view of a key portion of the jet shooting device of FIG. 2, the longitudinal section of each hole 15 and 16 is orthogonal to the circumferential surface 12c of the jet nozzle member 12 to such an extent as to allow the wall of the jet nozzle member to be punched at the manufacturing stage.

Figure 5:
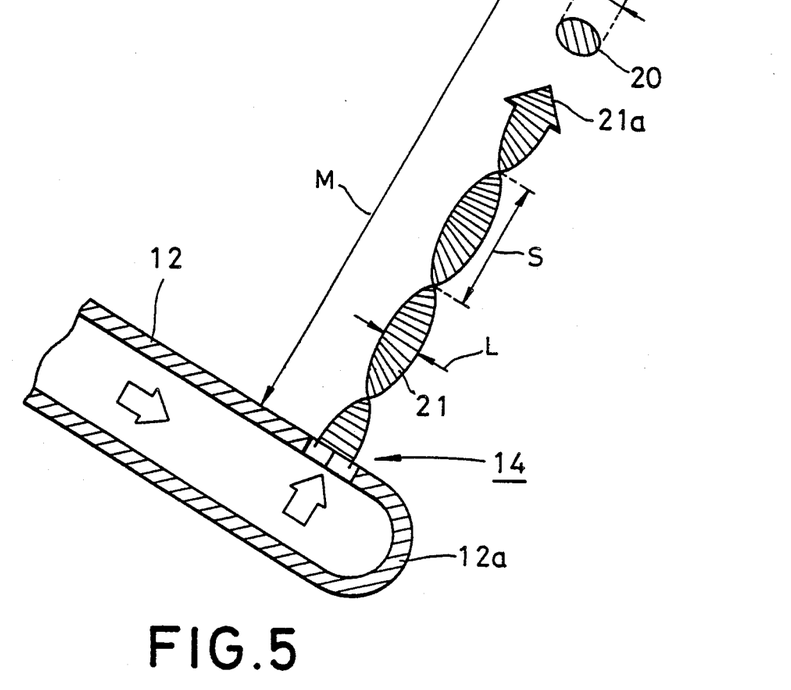
FIG. 5 is a sectional view showing a key portion of a jet shooting device according to the present invention, the illustration being for explaining the operation of the nozzle member.

To use the shooting device 10, the jet nozzle 14 of the nozzle member 12 is set under and in alignment with an object 20, e.g.,anal (FIG. 5). Then, an operator forcefully gasps the container 11 (FIG. 1) containing washing medium (hot water at about 40° C., in this instance) to deform it. In turn, the resultant high pressure hot water within the nozzle member 12 is shot from the nozzle member 14, and travels toward the object 20. At this time, as indicated by an arrow, the jet 21 jetted from the nozzle member 14 is shaped like a strip 21 of jet traveling with a spiral rotation, at the start of its shooting. The jet strip, with the increased straight drive, forcefully travels toward the object 20. The width L and the pitch S of the spiral turn of the jet 21 are almost invariable up to a point in close proximity to the object (although it may vary for specific figures of the size of the jet nozzle or the pressure applied).

An experiment was conducted by using the jet shooting device incorporating the thus constructed nozzle member in the following condition: distance M between the nozzle member surface and the object 20 is 1 m; diameter F of each of the paired holes 15 and 16, 1.2 mm; pitch E between the holes 15 and 16, 1.0 mm; and width W of the slit-like hole 17, approximately 0.5 mm. Under this condition, the container 11 was forcefully grasped to press the contained medium and to shoot forth the jet strip 21 toward the object 20. The result of the experiment showed that the width N of the strip 21 of jet was approximately 5 mm at a place of the object 20. It was found that there was little difference between this figure and that of the strip width of the jet water just after it is jetted. This fact indicates that the jet strip 21 little expand at the leading end 21a of the jet, and hence the jet 21 may concentrically hit the object 20.

It is noted that since the jet nozzle 14 is almost orthogonal to the circumferential surface 12c of the jet nozzle member 12, as shown in FIG. 3, the nozzle member as manufactured by using a metal mold may readily be punched to form the nozzle 14. Therefore, the jet nozzle 14 and the nozzle member 12 may be formed by using a metal mold, in one manufacturing step.

Figure 4:
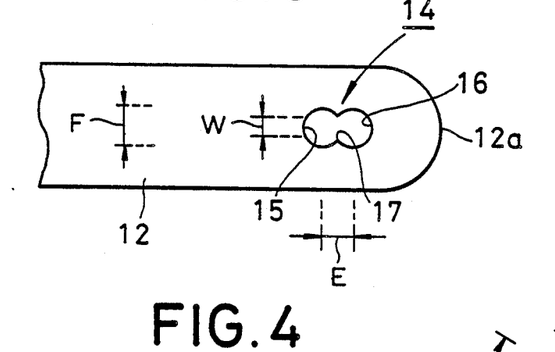
FIG. 4 is an enlarged plan view of a key portion of the jet shooting device of FIG. 1.
Figure 6:
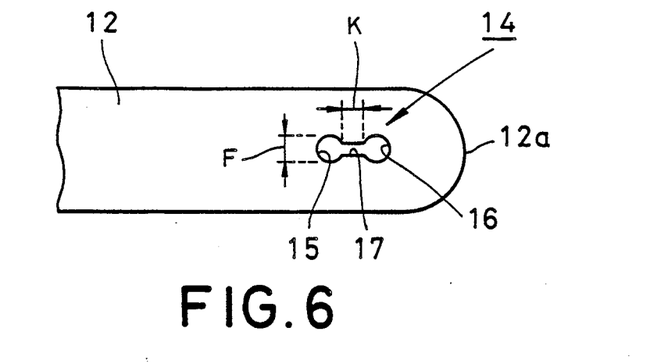
FIG. 6 is a plan view showing a key portion of another embodiment of the present invention.
Figure 7:
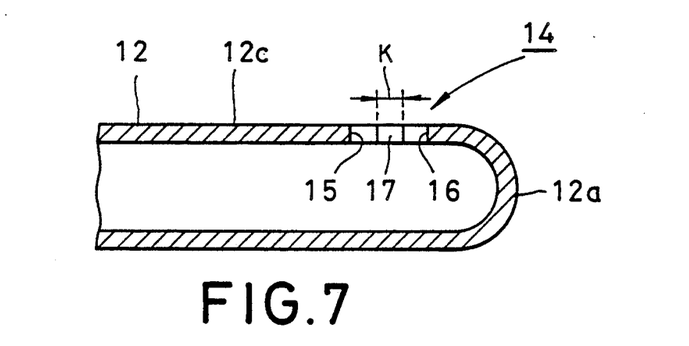
FIG. 7 is a sectional view of the diagram of FIG. 6.

In the above embodiment, a length of the hole 17 between the paired holes is almost zero as shown in FIG. 4. If necessary, the length K of the slit-like hole 17 constituting the nozzle 14 may be any of figures within the length two times the diameter F of each of the holes 15 and 16, in accordance with the type of an object to which the shooting device is applied (for example, the applied object has a large configuration), as shown in FIG. 6 in which like portions are designated by like reference symbols in FIG. 4, and in FIG. 7 showing a sectional view of the drawing of FIG. 6. (If the length K of the slit-like hole 17 exceeds the length two times the diameter F of each hole 15 and 16, the jet strip is apt to expand in width at the leading end). Incidentally, if the length K of the slit-like hole 17 is increased, the width L of the strip 21 shown in FIG. 5 becomes wide, and a velocity of the traveling jet 21 is decreased.

While in the above-mentioned embodiment, one jet nozzle 14 is used for one nozzle member 12, it is evident that a plurality of jet nozzles 14 of properly selected different lengths K may be formed in one nozzle member 12, and these may be selectively used.

Figures 8, 9:
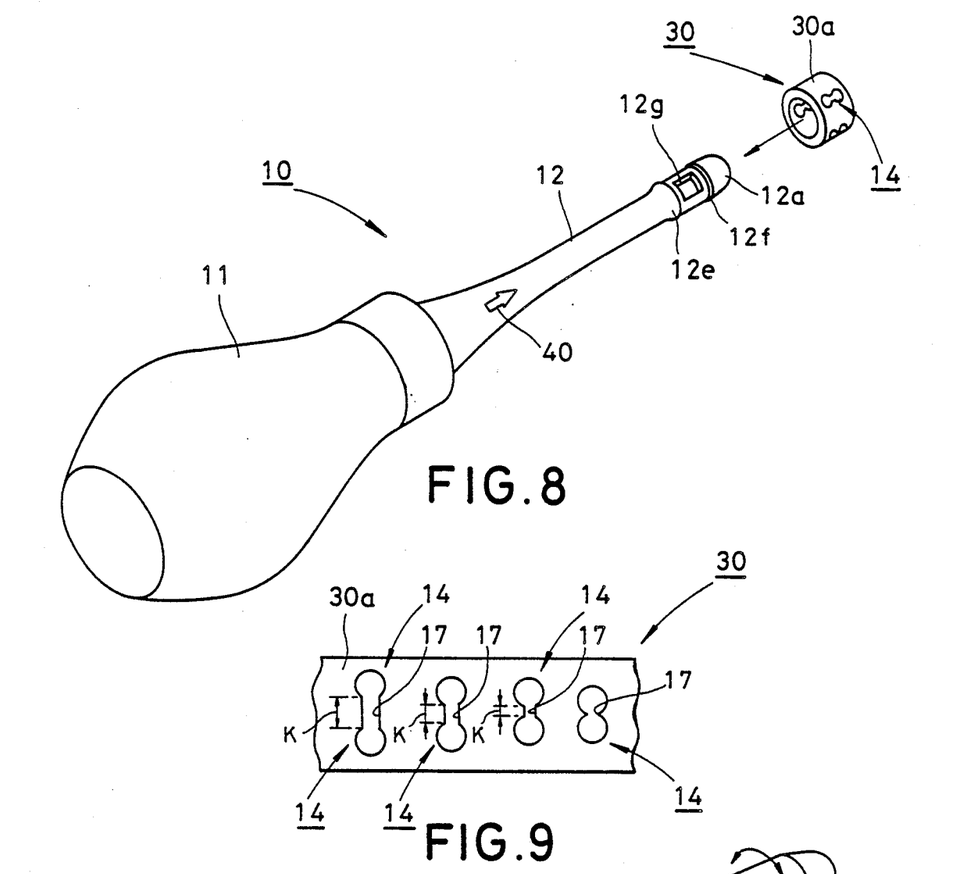
FIG. 8 is a schematic diagram showing yet another embodiment of the present invention.
FIG. 9 is a developement of a ring.

FIG. 8 is an exploded, perspective view showing another embodiment implementing the above technical idea, in which like portions are designated by like reference symbols in FIG. 1.

Figure 10:
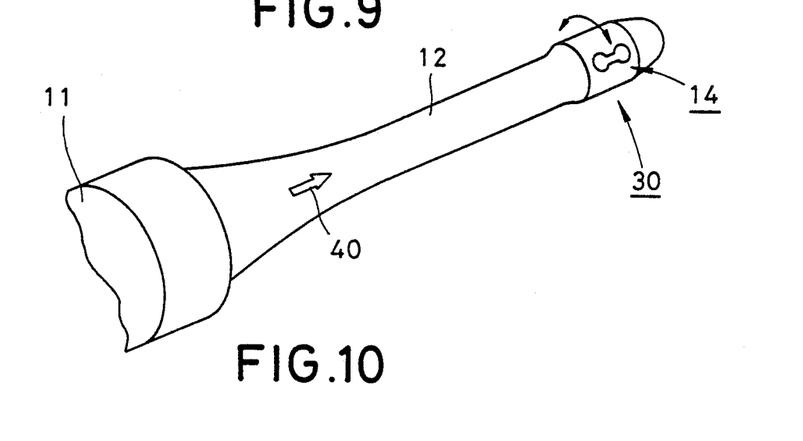
FIG. 10 is a sectional view showing a key portion of the jet shooting device of FIG. 8.

Two larger diameter portions 12e and 12f, spaced at a predetermined distance, are formed in the nozzle member 12 of the jet shooting device 10. A rectangular hole 12g, whose area is equal to or larger than that of the nozzle 14, is formed in the circumferential surface of a smaller diameter portion located between those larger diameter portions 12e and 12f. Further, the shooting device 10 uses a ring 30 of a certain width, which is to be fitted around the smaller diameter portion between the larger diameter portions 12e and 12f. The circumferential surface 30a of this ring 30 has a plurality of jet nozzles 14 arranged at predetermined pitches, as shown in FIG. 9 as a development of the ring. In the nozzles 14, the slit-like holes 17 constituting the nozzles 14 have different lengths K. The ring 30 thus structured is set around the nozzle member 12 and turned in either of the directions of arrow, as shown by an exploded, perspective view of a key portion of the shooting device as illustrated in FIG. 10 so that any of the nozzles 14 is located just above the rectangular hole 12g shown in FIG. 8. In this way, a proper jet nozzle 14 may be selected, which is most suitable for an object to which the shooting device is currently applied. From the selected nozzle 14, a jet water strip of the width defined by the selected nozzle is projected toward the object.

In FIGS. 1, 8 and 10, reference symbols 40 designates an arrow mark raised from the surface of the nozzle member 12 for indicating the location of the nozzle 14.

Figure 11:
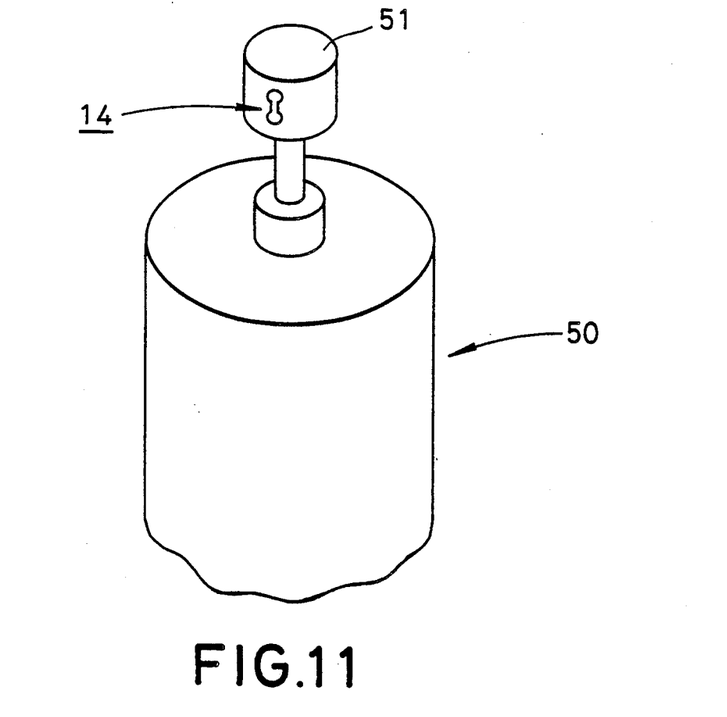
FIG. 11 is a schematic perspective view showing still another embodiment of the present invention.
Figure 12:
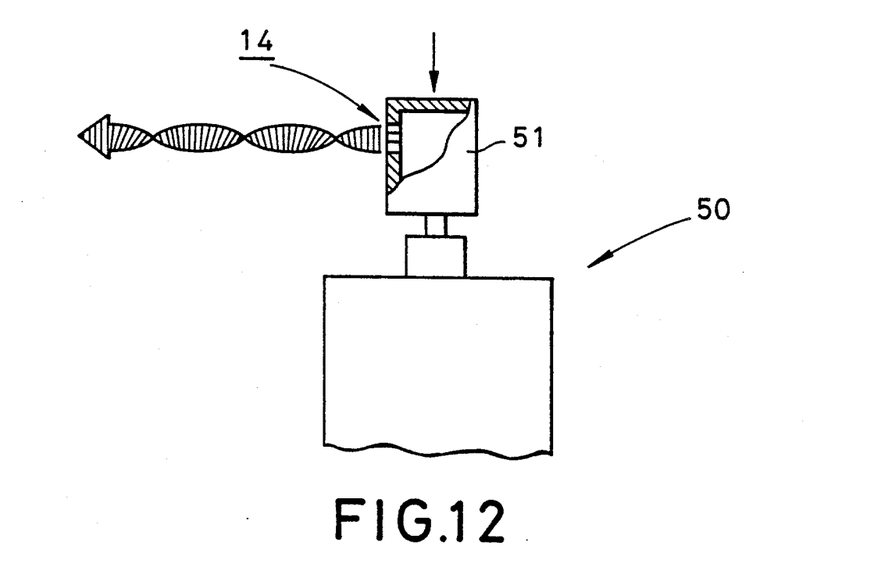
FIG. 12 is a cutaway view showing a key portion of the device of FIG. 11.

In the above-mentioned embodiments, the nozzle member according to the present invention is applied to the shooting device for shooting forth a jet of washing water, which is used mainly for washing an anal. It is evident, however, that the present invention is not limited to those embodiments, but is applicable for other spraying devices. For example, the present invention is applicable for a jet nozzle member 51 of a jet shooting device or sprayer 50 for concentrically shooting forth a jet medium toward an object with the aid of the pressure of Freon gas, for example, as shown in FIG. 11 and FIG. 12 showing a cutaway view of a key portion of the device of FIG. 11. Essentially, the present invention is applicable for any jet shooting device 50 if it projects a jet medium toward an object concentrically, not dissipatedly.

Figure 6A:
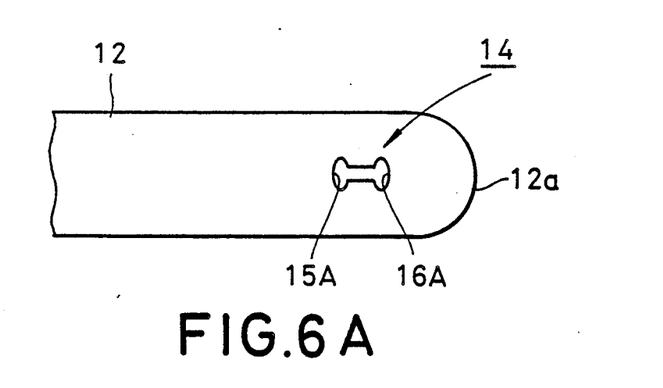
FIG. 6A is a plan view showing a key portion of still another embodiment of the present invention.

In the above-mentioned embodiments, the paired holes 15 and 16 distanced at a predetermined pitch are each circular in shape, in order to ease the punching work to form the holes. If required, those holes may be elliptic, as shown at 15A and 16A in FIG. 6A.

As described above, the nozzle member according to the present invention is capable of shooting a spirally turning jet strip of liquid or gas medium at the start of its shooting. Therefore, the jet may be highly concentrically applied to an object. Further, the longitudinal section of the nozzle member is substantially orthogonal to the nozzle member. This feature allows the jet nozzle and the nozzle member to be formed by a metal mold in one manufacturing step. Consequently, the manufacturing process is simplified, the production yield is improved, and hence the cost to manufacture is reduced.

Having described some specific embodiments of our bearing, it should be understood that the present invention may variously be changed and modified within the spirit and scope as set forth in the appended claims. It is further understood that the variations and modifications within the equivalents of the invention as defined in the claims are also within the spirit and scope of the invention.

What is claimed is:

1. A jet shooting device comprising:
   nozzle means for shooting a jet of washing liquid having a spiral rotation toward an object, said nozzle means including a pair of circular holes of same diameter and a slit with a width at least equal to or smaller than said same diameters through which said pair of circular holes intercommunicate with each other,
   a container containing said washing liquid, and
   a tubular nozzle member coupled with said container and having said nozzle means formed in a circumferential surface of a closed end thereof.

2. The jet shooting device according to claim 1, wherein said container is opened at one end and is made of a flexibly deformable resilient material, and said tubular nozzle member is made of a rigid macromolecular material.

3. A jet shooting device comprising a tubular nozzle member and nozzle means for shooting a jet of fluid having a spiral rotation toward an object, said nozzle means including a pair of elliptical holes having their openings orthogonal to an axial direction of said tubular nozzle member and a slit with a width at least equal to or smaller than widths of said elliptical holes through which said pair of elliptical holes intercommunicate with each other.

4. A nozzle member with a jet nozzle for shooting forth a jet medium toward an object, in use with a jet shooting device, said nozzle member comprising a closed end portion with two larger diameter portions arranged with a smaller diameter portion therebetween, a rectangular hole arranged within said smaller diameter portion, and a ring arranged about said smaller diameter portion and having a width sufficient for covering said rectangular hole, said ring having a plurality of jet nozzles at predetermined pitches on a circumferential surface thereof, each of said jet nozzles having a pair of circular holes of same diameter and a slit with a width at least equal to or smaller than said same diameters connecting said pair of circular holes, each said slit of said plurality of nozzles having a length different from other of said slits within a length of two times said same diameters.

5. The nozzle member according to claim 4, wherein said shooting device includes a container communicating with said nozzle means and having said fluid therein, and said fluid is a washing liquid for washing an anal.

6. The nozzle member according to claim 4, wherein said shooting devices includes a container communicating with said nozzle means and having said fluid therein, and said fluid is hot water.

7. The nozzle member according to claim 4, wherein said shooting device includes a container having said jet medium therein and a tubular nozzle member coupled with said container, and said jet medium is a washing liquid.

8. The jet shooting device according to claim 7, wherein said container is opened at one end and made of a flexibly deformable resilient material, and said tubular nozzle member is made of a rigid macromolecular material.

9. The jet shooting device according to claim 4, wherein internal circumferential walls of said pair of circular holes and said slit are orthogonal to a circumferential surface of said nozzle member.

* * * * *